United States Patent [19]

Katsumata et al.

[11] Patent Number: 4,954,441

[45] Date of Patent: Sep. 4, 1990

[54] PROCESS FOR PRODUCING L-LYSINE

[75] Inventors: Ryoichi Katsumata; Toru Mizukami, both of Machida; Tetsuo Oka, Yokohama, all of Japan

[73] Assignee: Kyowa Hakko Kogyo Co. Ltd., Tokyo, Japan

[21] Appl. No.: 356,614

[22] Filed: May 25, 1989

Related U.S. Application Data

[63] Continuation of Ser. No. 836,989, Mar. 6, 1986, abandoned.

[30] Foreign Application Priority Data

Mar. 12, 1985 [JP] Japan .................................. 60-47515

[51] Int. Cl.$^5$ .......................... C12N 1/21; C12N 9/88; C12N 15/03; C12N 15/31
[52] U.S. Cl. .................... 435/115; 435/69.1; 435/116; 435/172.1; 435/172.3; 435/170; 435/252.32; 435/840; 435/843; 435/232; 536/27
[58] Field of Search .................. 435/172.1, 172.3, 115, 435/116, 840, 843, 69.1, 232, 170, 252.32; 935/29, 60, 72, 6, 9, 10, 22, 42; 536/27

[56] References Cited

U.S. PATENT DOCUMENTS

| | | | |
|---|---|---|---|
| 4,495,283 | 1/1985 | Araki et al. | 435/107 |
| 4,560,654 | 12/1985 | Miwa et al. | 435/115 |
| 4,601,983 | 6/1984 | Nakamori et al. | 435/115 |
| 4,861,722 | 8/1989 | Sano et al. | 435/252.32 |

FOREIGN PATENT DOCUMENTS 0088166 9/1983 European Pat. Off. .
2482622 11/1981 France .

OTHER PUBLICATIONS

Richard et al., CR Seances Acad. Sci., Ser. 3, 1981, 293(9), CA 96, 194398n, 507–512 (1981).
Simms et al, J. Biol. Chem. (1984), vol. 259, #5, pp. 2734–2741.

Primary Examiner—Richard A. Schwartz
Assistant Examiner—Richard C. Peet
Attorney, Agent, or Firm—Fitzpatrick, Cella, Harper & Scinto

[57] ABSTRACT

A process for producing L-lysine is disclosed in which a recombinant vector, a DNA fragment of which contains a gene involved in the synthesis of dihydropicolinic acid synthetase, is used to transform a microorganism of the genus Corynebacterium or Brevibacterium. The transformant is then cultured in a medium which supports the accumulation of L-lysine. Subsequently the L-lysine is recovered from the culture broth.

6 Claims, 1 Drawing Sheet

PROCESS FOR PRODUCING L-LYSINE

BACKGROUND OF THE INVENTION

This invention relates to a process for producing L-lysine, which comprises introducing a recombinant DNA of a DNA fragment containing a gene involved in the synthesis of dihydrodipicolinic acid synthase (hereinafter referred to as DDPS) or tetrahydropicolinic acid succinylase (hereinafter referred to as THPS), and a vector DNA into a microorganism belonging to the genus Corynebacterium or Brevibacterium, culturing the microorganism in a medium and recovering L-lysine accumulated in the cultured broth. Thus, the present invention relates to the field of bioindustry, and particularly to the field of producing L-lysine which is useful as a feed additive in the livestock industry.

Improvement of the so-called glutamic acid-producing microorganisms such as microorganisms of the genera Corynebacterium and Brevibacterium by recombinant DNA technology to increase L-lysine productivity is disclosed in Japanese Published Unexamined Patent Application Nos. 160997/81, 126789/83, etc.

Improving the process for producing a large amount of L-lysine using microorganisms is a continual problem. The present invention provides a solution to the problem by more effectively utilizing recombinant DNA technology.

The present inventors have found that a productivity of L-lysine can be improved by the use of a strain harboring a recombinant plasmid vector containing a gene involved in the synthesis of DDPS or THPS responsible for the biosynthesis of L-lysine.

SUMMARY OF THE INVENTION

This invention relates to a process for producing L-lysine, which comprises introducing a recombinant vector a DNA fragment of which contains a gene involved in the synthesis of DDPS or THPS, into a microorganism belonging to the genus Corynebacterium or Brevibacterium, culturing the microorganism in a medium and recovering L-lysine accumulated in the cultured broth.

DESCRIPTION OF THE INVENTION

Figure 1:
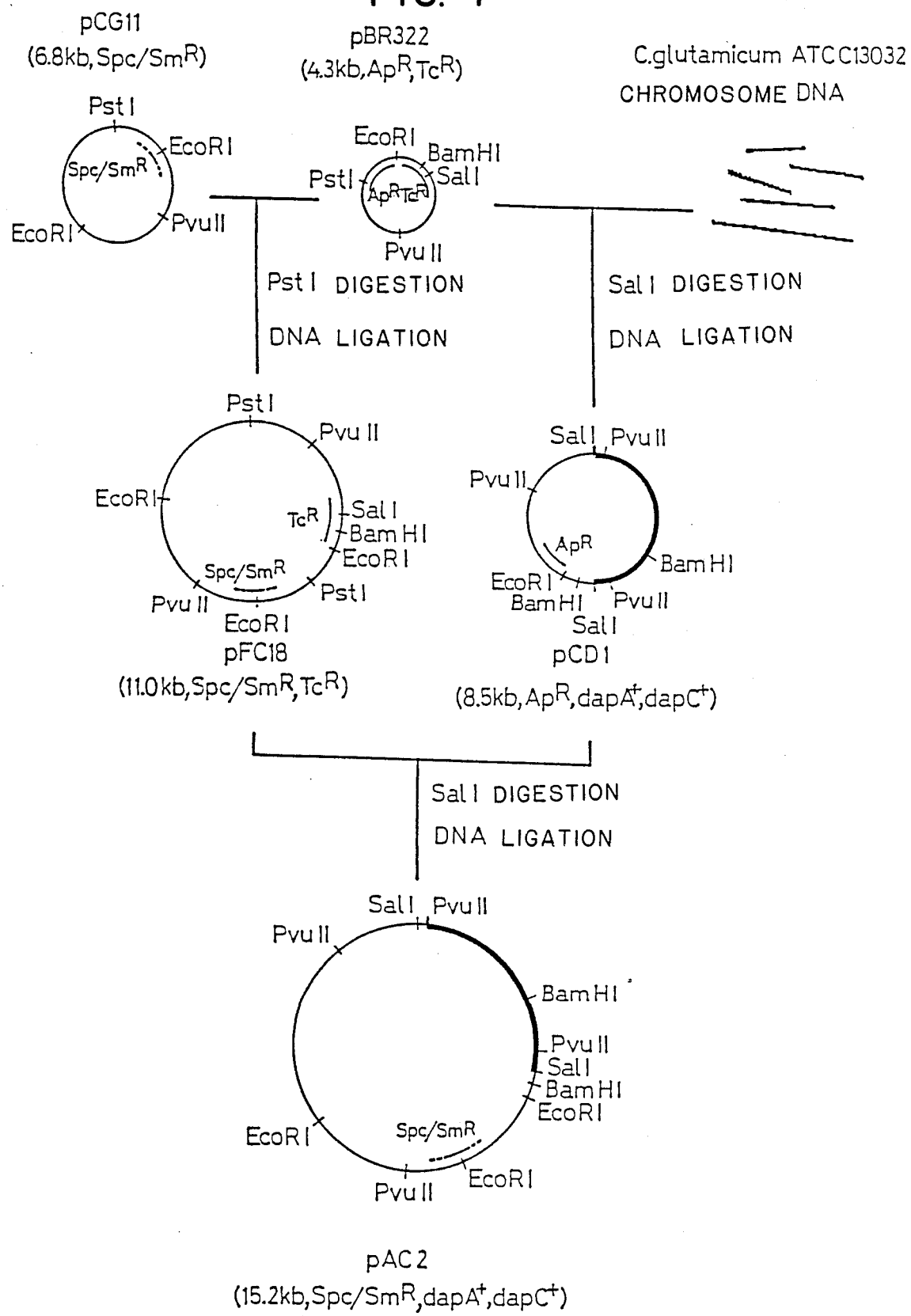
FIG. 1 is a flow sheet showing a process for preparing vector plasmid pFC18, where Spc/Sm show resistance markers of spectinomycin and streptomycin, Ap that of ampicillin, and Tc that of tetracycline.

According to the present invention, L-lysine can be produced by culturing in a medium a microorganism belonging to the genus Corynebacterium or Brevibacterium harboring a recombinant vector of a DNA fragment of which contains a gene involved in the synthesis of DDPS or THPS, accumulating L-lysine in the cultured broth, and recovering L-lysine therefrom.

As the microorganism belonging to the genus Corynebacterium or Brevibacterium to be used as a host microorganism, any of the microorganisms known as the so-called glutamic acid-producing microorganisms can be used. Preferably, the following strains can be used.

| | |
|---|---|
| Corynebacterium glutamicum | ATCC 13032 |
| Corynebacterium acetoacidophilum | ATCC 13870 |
| Corynebacterium herculis | ATCC 13868 |
| Corynebacterium lilium | ATCC 15990 |
| Brevibacterium divaricatum | ATCC 14020 |
| Brevibacterium flavum | ATCC 14067 |
| Brevibacterium immariophilium | ATCC 14068 |
| Brevibacterium lactofermentum | ATCC 13869 |
| Brevibacterium thiogenitalis | ATCC 19240 |

Wild-type lysine non-producing strains can be used as the host microorganism, but lysine producing strains can also be used. As a lysine-producing strain, known strains such as amino acid-requiring mutant strains, amino acid analog-resistant mutant strains, etc. are applicable.

As the gene involved in the synthesis of DDPS or THPS, any of those derived from eukaryotes, prokaryotes, viruses, bacteriophages or plasmids can be used. The gene of a strain belonging to a prokaryote bacterium, for example, of the genus Escherichia, Corynebacterium, Brevibacterium, Microbacterium, Bacillus, Staphylococcus, Streptococcus, or Serratia, is preferable. The gene derived from a lysine-producing mutant strain belonging to these bacteria is particularly preferable.

As the vector for incorporating the DNA fragment containing the gene, pCG1, pCG2, pCG4, pCG11, pCE54, pCB 101, etc. developed by the present inventors are preferably used. Processes for producing these vectors are described in Japanese Published Unexamined Patent Application Nos. 82, 183799/82, 35197/83 and 105999/83.

The recombinant vector a DNA of which contains the gene involved in the synthesis of DDPS or THPS, can be obtained according to recombinant DNA technology which comprises cleaving in vitro both DNAs with restriction enzymes, recombining the cleaved DNAs with a DNA ligase, transforming a mutant strain belonging to the genus Corynebacterium or Brevibacterium and defective in the DDPS or THPS gene with the ligation mixture, and selecting the transformants wherein the lysine producing phenotype is restored. The recombinant DNA technology can be carried out according to the procedures described in Japanese Published Unexamined Patent Application Nos. 186492/82 and 186489/82.

Instead of cloning the recombinant DNA directly in a nucriirgabusn belonging to the genus Corynebacterium or Brevibacterium, the recombinant vector DNA can also be obtained by using another well established host-vector system as exemplified by Escherichia coli system. That is, cloned DNA fragments containing the gene can be obtained from the transformants prepared by the method which comprises transforming an Escherichia coli mutant which lacks the gene involved in the synthesis of DDPS or THPS with the in vitro ligation mixture of the donor DNA and the vector DNA, and selecting transformants wherein the lysine producing phenotype is restored. By recombining the DNA with the vector DNA of a bacterium of the genus Corynebacterium or Brevibacterium in vitro, thereby transforming the bacterium of the genus Corynebacterium or Brevibacterium, it is possible to have the bacterium contain the cloned recombinant DNA containing the gene.

The present invention is explained more in detail below, referring to a gene involved in the synthesis of DDPS of Corynebacterium glutamicum (hereinafter referred to as DDPS gene or dapA) and a gene involved in the synthesis of THPS of *Corynebacterium glutamicum* (hereinafter referred to as THPS gene or dapC).

A DNA fragment containing dapA and dapC of *Corynebacterium glutamicum* can be cloned in advance by the host-vector system of *Escherichia coli*. A procedure for cloning a gene with *Escherichia coli* as a host is described, for example, in Method in Enzymology, Volume 68, edited by Ray Wu and published by Academic Press, New York (1979) Specifically, the procedure is as follows:

A chromosome DNA extracted from *Corynebacterium glutamicum* ATCC 13032, and *Escherichia coli* vector plasmid pBR322 (having a resistance to ampicillin and tetracycline) are cleaved by a restriction enzyme SalI, and then recombined by a DNA ligase of phage T4.

Substrain TM103 of *Escherichia coli* K12 [hsdR-(host-specific restriction-defective) and dapA- (DDPS-defective: diaminopimelic acid-requiring)] is transformed by the recombined product, and the transformants capable of growing on a minimal medium containing ampicillin are selected. The contained plasmid can be separated from the cultured cells of the transformant not requiring diaminopimelic acid and resistant to ampicillin according to conventional methods. Further, the plasmid DNA is cleaved with restriction enzymes and the thus formed DNA fragments are analyzed by agarose gel electrophoresis, whereby their structure can be determined. One of the thus obtained plasmids is pCD1. pCD1 has such a structure that a SalI DNA fragment of 4.2 kilobases(Kb) is inserted in the unique SalI cleavage site of pBR322 (FIG. 1).

None of the ampicillin-resistant transformants obtained by transforming DDPS-defective mutant strain AT998 (Hfr dapA16) and THPS-defective mutant strain AT997 (Hfr dapC15) which are substrains of *Escherichia coli* [J. Bacteriol. 105, 844 (1971)] respectively with pCD1 DNA require diaminopimelic acid and from this fact, it is obvious that the 4.2Kb SalI DNA fragment of pCD1 contains the genes dapA and dapC of *Corynebacterium glutamicum* coding for the function to restore the DDPS and THPS defects of *Escherichia coli*.

So-called shuttle-type recombinant plasmid pAC2 which is replicable in the microorganism of the genera Corynebacterium, Brevibacterium and Escherichia is formed by inserting in the unique SalI cleavage site of plasmid pFC18 (having a resistance to tetracycline and a resistance to spectinomycin) the SalI DNA fragment of 4.2 Kb containing dapA and dapC cloned on pCD1. pFC18 plasmid is a shuttletype vector plasmid prepared by inserting in the PstI cleavage site of vector plasmid pBR322 of *Escherichia coli* vector plasmid pCG11 of the genera Corynebacterium and Brevibacterium previously found by the present inventors Japanese Published Unexamined Patent Application No. 34500/82]. The process for preparing the said plasmid and its structure are shown in FIG. 1.

pAC2 plasmid is prepared according to the following steps.

pFC18 and pCD1 plasmid DNAs are cleaved with a restriction enzyme SalI, then mixed together and subjected to the action of T4 ligase. Then, substrain TM103 of *Escherichia coli* K12 having DDPS-defect is transformed with the ligation mixture, and the transformants grown on a minimal medium containing spectinomycin are selected. A plasmid DNA is extracted from the cultured cells of one of the thus obtained transformants having resistance to spectinomycin and not requiring diaminopimelic acid.

The separated SalI cleavage product of the plasmid DNA is subjected to agarose gel electrophoresis to investigate the structure of the plasmid. It is confirmed that the plasmid has such a structure that the SalI DNA fragment of 4.2 Kb derived from pCD1 is inserted in the Sal I cleavage site of pFC18 vector plasmid. Then, DDPS-defective mutant strain AT998 and THPS-defective mutant strain AT997 which are substrains of *Escherichia coli* K12 strain, are transformed with the said plasmid, and because the defect in each of the mutants is restored, it is confirmed that dapA and dapC of *Corynebacterium glutamicum* once cloned in pCD1 are incorporated in the said plasmid; that plasmid is named pAC2 (FIG. 1).

*Corynebacterium glutamicum* RH 6 strain, a lysine-producing microorganism having a homoserine-requirement induced by mutation (the strain is deposited as FERM-BP 704 in Fermentation Research Institute, Agency of Industrial Science and Technology) is transformed with pAC2 plasmid. The transformation can be carried out according to a transformation method using protoplast of a strain of the genus Corynebacterium or Brevibacterium previously found by the present inventors, for which patent applications were filed [Japanese Published Unexamined Patent Application Nos. 186492/82 and 186489/82]. The protoplast of *Corynebacterium glutamicum* RH6 strain is transformed according to the said method, and then transformants are selected on a regeneration medium containing spectinomycin. The plasmid separated from the cultured cells of one of the thus obtained spectinomycin-resistant transformants is subjected to the structure investigation by the same restriction enzyme cleavage and agarose gel electrophoresis as described in the preceding paragraph, and also to the confirmation of the presence of dapA and dapC according to transformation test of substrains AT998 and AT997 of *Escherichia coli* K12 strain. It is confirmed that pAC2 plasmid is introduced into RH6 strain.

The production of L-lysine by pAC2 transformant can be carried out according to a culturing method used in the conventional process for producing L-lysine by fermentation. That is, when the transformant is cultured in a conventional medium containing a carbon source, a nitrogen source, inorganic matters, amino acids, vitamins, etc. under aerobic conditions, while controlling the temperature, pH, etc., lysine is formed and accumulated in the culture broth. Thus, L-lysine can be recovered from the culture broth according to known methods, for example, by active carbon treatment, ion exchange resin treatment, etc.

Thus, L-lysine can be produced in a higher yield by using a pAC2-containing strain of the genus Corynebacterium or Brevibacterium than by using a strain which does not contain pAC2. The usefulness of the present invention lies in an endowment or an enhancement of productivity of L-lysine by introducing a recombinant DNA in which the DDPS and/or THPS genes and a vector of a strain of the genus Corynebacterium or Brevibacterium are recombined in a form capable of expressing the character, into a strain of the genus Corynebacterium or Brevibacterium. In the present specification, an example of using the genes involved in the synthesis of DDPS or THPS derived from *Corynebacterium glutamicum* is shown. Lysine productivity of lysine-producing microorganisms can also be improved when the corresponding genes of other organisms are used in place of the said genes.

The vector plasmid only provides an autonomous replicability for stable inheritance of genes involved in the synthesis of recombined DDPS or THPS. Thus, not only pFC18 exemplified in the present specification, but also other plasmids autonomously replicable in a microorganism of the genus Corynebacterium or Brevibacterium and phage vectors capable of stable inheritance by being inserted components of a chromosome of the host can be used.

In spite of many common microbiological properties, microorganisms with high glutamic acid productivity (so-called glutamic acid-producing microorganisms) are classified to various species by researchers and even genera such as Corynebacterium and Brevibacterium probably because of their industrial importance. However, it has been pointed out that these microorganisms should be classified as one species because they have homology in the amino acids in the cell walls and the GC content of DNA. Recently, it has been reported that these microorganisms have more than 70% -80% homology in DNA-DNA hybridization, indicating that the microorganisms are very closely related [see: Komatsu, Y.: Report of the Fermentative Research Institute, No. 55, 1 (1980), and Suzuki, K., Kaneko, T., and Komagata, K.: Int. J. Syst. Bacteriol., 31, 131 (1981)].

In the present specification, a case where a recombinant DNA is introduced into Corynebacterium glutamicum RH6, and where the improvement in L-lysine production depends on the expression of the gene is given. Considering the above-mentioned very close relationship of glutamic acid-producing microorganisms, it is readily assumed that the present invention is applicable to all of the glutamic acid-producing microorganisms. The effect of the present invention depends on whether the recombinant DNA autonomously replicates in the glutamic acid-producing microorganism and whether the gene is expressed, and so slight difference of such DNA homology between glutamic acid-producing microorganisms are negligible. That the glutamic acid-producing microorganisms have the common function to allow replication of plasmids and expression of genes is apparent from the fact that plasmid pCG4 which is isolated from Corynebacterium glutamicum 225-250 (Japanese Published Unexamined Patent Application No. 183799/82) and which has spectinomycin and/or streptomycin resistance gene(s) can be generally replicated and expressed in glutamic acid-producing microorganisms such as strains of the genera Corynebacterium and Brevibacterium (Japanese Published Unexamined Patent Application No. 186492/82). Further, it has been shown by the present inventors that the tryptophan-biosynthesizing gene of a bacteria of the genus Brevibacterium can be expressed in a bacteria of the genus Corynebacterium, and the histidine-biosynthesizing gene of a bacteria of the genus Corynebacterium can be expressed in a bacteria of the genus Brevibacterium (Japanese Published Unexamined Patent Application Nos. 25398/83 and 25397/83). Thus, it is apparent that the genes can be mutually expressed between the bacteria of these two genera. Accordingly, the bacteria to which the present invention is applicable include not only Corynebacterium glutamicum, but also all the glutamic acid-producing microorganisms including the bacteria of the genera Corynebacterium and Brevibacterium.

Certain specific embodiment of the present invention are illustrated by the following representative examples.

EXAMPLE 1

(1) Construction of a substrain TM103 of Escherichia coli K12 having host-specific restriction-deficient mutation and DDPS-deficient mutation:]

To more readily clone a gene involved in the synthesis of DDPS of Corynebacterium glutamicum, which is a foreign gene, in a host-vector system of Escherichia coli, a strain of Escherichia coli having host-specific restriction-deficient mutation (hsdR$^2$-) and DDPS-deficient mutation (dapA 16-) simultaneously was constructed as a host microorganism in the following manner.

From a substrain WA802 of Esherichia coli K12 having a restriction-deficient mutation (Escherichia coli K12 WA802, FERM BP-718) [F- met B1 hsd R$^2$: J. Mol. Biol. 16 118 (1966)] was derived a spontaneous mutant strain RF82 having a resistance to 25μg/ml of rifampicin. The strain RF82 and a DDPS-defective mutant strain AT998 (Hfr dapA16) (Escherichia coli K12 AT998, FERM BP-720) were cultured in L medium [1% bactotrypton (Difco), 0.5% yeast extract (made by Daigo Eiyo Kagaku K.K., Japan), and 0.5% NaCl, adjusted to pH 7.0 with NaOH) containing 50μg/ml of diaminopimelic acid at 37° C. for 3 hours. After washing twice with a physiological saline solution by centrifugation, the washed cells were spread on M9 minimal agar plate medium (a medium containing 2 g of glucose, 1 g of NH$_4$Cl, 6 g of Na$_2$HPO$_4$, 3 g of KH$_2$PO$_4$, 0.1 g of MgSO$_4$.7H$_2$O, 15 mg of CaCl$_2$.2H$_2$O, 4 mg of thiamine hydrochloride and 15 g of agar in 1 l of water and adjusted to pH 7.2) containing 25 μg/ml of rifampicin and 50 μg/ml of diaminopimelic acid, and transconjugants having resistance to rifampicin and not requiring methionin were selected. Strains showing diaminopimalic acid requirement and having restriction-deficient mutation were selected from the transconjugants, and one such strain was designated as TM103. The presence of restriction-deficient mutation was determined by the plating efficiency of λ phage propagated on the strain C600r-m- (ATCC 33525), a modificationdeficient Eschrichia coli K12 strain [M. Meselson J. Mol. Biol., 9 734 (1964)]. λ Phage was prepared from Escherichia coli K12 λ lysogenic bacterium ATCC 10798 according to a conventional method. That is, a strain showing the same plating efficiency as that of WA802 was regarded as a transconjugant having a restriction-deficient mutation.

(2) Cloning of DDPS gene (dapA) of Corynebacterium glutamicum

Cloning was carried out by a host-vector system of Escherichia coli. pBR322 used as a vector was a commercially available product made by Takara Shuzo Co., Japan. Chromosome DNA used as a donor DNA was isolated from Corynebacterium glutamicum ATCC 13032 according to a procedure previously disclosed by the present inventors [Japanese Published Unexamined Patent Application No. 126789/83, Example 1, Item (1)].

To 120 μl of a reaction solution for the restriction enzyme SalI (10 mM Tris-HCl, 7 mM MgCl$_2$, 100 mM NaCl, pH 7.5) containing 4 μg of pBR322 DNA and 8 μg of chromosome DNA of Corynebacterium glutamicum was added 12 units of SalI (product of Takara Shuzo Co., Japan). The mixture was subjected to reaction at 37° C. for 60 minutes, and the reaction was discontinued after heating at 65° C. for 10 minutes. To the reaction digested product were added 30 μl of T4 ligase buffer solution (660 mM Tris-HCl, 66 mM MgCl2, 100 mM dithiothreitol, pH 7.6), 30 μl of 5 mM ATP, 0.3 units of T4 ligase (product of Takara Shuzo Co., Japan), and 120 μl of H2O. The mixture was subjected to reaction at 12° C. for 16 hours.

The ligase reaction mixture was subjected to transformation of substrain TM103 of *Escherichia coli* K12 Competent cells of TM103 were prepared according to the method of Dagert et al [Dagert, M. et al: Gene 6, 23 (1979)]. That is, TM103 strain was inoculated in 50 ml of L medium supplemented with 50 μg/ml of diaminopimelic acid and cultured at 37° C. until the absorbancy (OD) at 660 nm reached 0.5 by Tokyo Koden colorimeter. The culture liquid was cooled in ice water for 10 minutes, and then the cells were collected by centrifugation and suspended in 20 ml of cooled 0.1 M calcium chloride The suspension was kept at 0° C. for 20 minutes. The cells were collected by centrifugation and resuspended in 0.5 ml of 0.1 M calcium chloride The suspension was left standing at 0° C. for 18 hours. To 400 μl of the suspension was added 200 μl of the ligase reaction mixture prepared above, and the mixture was kept at 0° C. for 10 minutes and then heated at 37° C. for 5 minutes Then, 9 ml of L medium containing 50 μg/ml diaminopimelic acid was added thereto, and the mixture was subjected to shaking culture at 37° C. for 2 hours. The cultured cells were washed twice with a physiological saline solution by centrifugation, and spread on M9 minimal agar plate medium containing 50 μg/ml ampicillin, and cultured at 37° C. for 4 days. The thus obtained transformants having resistance to ampicillin and not requiring diaminopimelic acid were subjected to single colony isolation on L agar plate medium (L medium containing 1.5% agar) containing 50 μg/ml ampicillin.

Plasmid DNA was isolated from the cultured cells of purified transformants according to the method of An et al [An, G. et al: J. Bacteriol., 140 400 (1979)]. The plasmid DNA was digested with restriction enzymes and analyzed by agarose gel electrophoresis, and it was found that the plasmid DNA had such a structure that the SalI DNA fragment of 4.2 Kb was inserted in the unique SalI cleavage site of pBR322. The plasmid was named pCD1.

pCD1 was subjected to transformation of DDPS-defective mutant strain AT998 and THPS-defective mutant strain AT997, which were substrains of *Escherichia coli* K12. Transformation of AT998 strain and AT997 strain (*Escherichia coli* K12 AT997, FERM BP-719) was carried out in the same manner as in the transformation of TM103 strain None of the transformants having a resistance to ampicillin obtained from these two strains required diaminopimelic acid. It is evident from these facts that not only DDPS gene (dapA) but also THPS gene (dapC) of *Corynebacterium glutamicum* exists on SalI DNA fragment of 4.2 Kb cloned on pCD1.

The restriction-deficient mutation possessed by the host microorganism, TM103 strain which was used in the cloning step was utilized merely to increase the frequency of cloning, and strains having no such mutation can be used as host microorganisms.

(3) Preparation of plasmid pAC2

SalI DNA fragment of 4.2 Kb containing dapA and dapC genes derived from *Corynebacterium glutamicum* was recloned by shuttle vector plasmid pFC18 (having a resistance to spectinomycin and a resistance to tetracycline). Preparation of pFC18 was carried out according to the following procedure.

pCG11 was isolated from a strain containing pCG11 (ATCC 39022) according to the procedure previously disclosed by the present inventors [Japanese Published Unexamined Patent application No. 134500/82, Example 1, Item (1)]. pBR322 used for this purpose was a commercially available product of Takara Shuzo Co., Japan To 120 μl of a reaction solution for the restriction enzyme PstI (20 mM Tris-HCl (pH 7.5), 10 mM MgCl2, 50 mM (NH4)2SO4 and 0.01% bovine serum albumin) containing 4 μg each of pCG11 and pBR322 plasmid DNAs was added 8 units of PstI (product of Takara Shuzo Co., Japan), and the mixture was subjected to reaction at 37° C. for 60 minutes. The reaction was discontinued after heating at 65° C. for 10 minutes. Then, 30 ml of T4 ligase buffer solution, 30 μl of 5 mM ATP, 0 3 units of T4 ligase and 120 μl of H20 were added thereto, and the mixture was subjected to reaction at 12° C. for 16 hours. Substrain WA802 of *Escherichia coli* K12 was transformed with the ligase reaction product according to the procedure shown in Example 1, Item (2). One of the transformants propagated on L agar plate medium containing 100 μg/ml spectinomycin and 25 μg/ml tetracycline was subjected to single colony isolation on the same agar medium, and plasmid DNA was isolated from the cultured cells of the purified strain according to the method of An et al. The structure of the plasmid DNA was investigated by restriction enzyme cleavage and agarose gel electrophoresis, and it was found that the plasmid DNA had such a structure that pBR322 was inserted in the unique pstI cleavage site of pCG11 (FIG. 1). The plasmid was named pFC18.

A recombinant plasmid containing dapA and dapC derived from *Corynebacterium glutamicum* was prepared, using pFC18 as a vector according to the following procedure containing 4 μg each of pFC18 and pCD1 plasmid DNAs was added 8 units of restriction enzyme SalI, and the mixture was subjected to reaction at 37° C. for 60 minutes. The reaction was discontinued after heating at 65° C. for 10 minutes, and then 30 μl of T4 ligase buffer solution, 30 μl of 5 mM ATP, 0.3 units of T4 ligase and 120 μl of H2O were added thereto. The mixture was subjected to reaction at 12° C. for 16 hours.

The ligase reaction product was subjected to transformation of *Escherichia coli* TM103 strain. Transformation was carried out according to the procedure shown in Example 1, Item (2), and transformants were selected on M9 minimal agar plate medium containing 100 μg/ml of spectinomycin. From one of the thus obtained transformants having a resistance to spectinomycin and not requiring diaminopimelic acid was isolated plasmid DNA according to the method of An et al. The structure of isolated plasmid DNA was investigated by restriction enzyme cleavage and agarose gel electrophoresis. It was found that the plasmid had such a structure that SalI DNA fragment of 4.2 Kb derived from pCD1 was inserted in the single SalI cleavage site of pFC18. The plasmid was named pAC2

Transformation of said AT998 and AT997 was carried out by pAC2, and it was confirmed that the spectinomycin-resistant transformants were complemented respectively by a diaminopimelic acid requirement at the same time.

(4) Introduction of pAC2 into *Corynebacterium glutamicum* RH6 strain.:

Transformation of *Corynebacterium glutamicum* RH6 strain (having a homoserine requirement) was carried out using pAC2.

0.1 ml of a seed culture of RH6 strain was inoculated in 10 ml of SSM medium (a medium containing 10 g of glucose, 4 g of $NH_4Cl$, 2 g of urea, 1 g of yeast extract, 1 g of $KH_2PO_4$, 3 g of $K_2HPO_4$, 0.4 g of $MgCl_2.6H_2O$, 10 mg of $FeSO_4.7H_2O$, 0.2 mg of $MnSO_4.4-6H_2O$, 0.9 mg of $ZnSO_4.7H_2O$, 0.4 mg of $CuSO_4.5H_2O$, 0.09 mg of $Na_2B_4O_7.10H_2O$, 0.04 mg of $(NH_4)_6 Mo_7O_{24}.4H_2O$, 30 µg of biotin, and 1 mg of thiamine hydrochloride in 1 l of water and adjusted to pH 7.2] containing 50 µg/ml homoserine, and subjected to shaking culture at 30° C. When OD reached 0.15, penicillin G was added thereto to make 0.5 units/ml. Culturing was further continued, and when OD reached about 0.6, the cultured cells were collected, and suspended in 2 ml of RCGP medium [a medium containing 5 g of glucose, 5 g of casamino acid, 2.5 g of yeast extract, 3.5 g of $K_2HPO_4$, 1.5 g of $KH_2PO_4$, 0.41 g of $MgCl_2.6H_2O$, 10 mg of $FeSO_4.7H_2O$, 2 mg of $MnSO_4.4-6 H_2O$, 0.9 mg of $ZnSO_4.7H_2O$, 0.04 mg of $(NH_4)_6Mo_7O_{24}.4H_2O$, 30 µg of biotin, 2 mg of thiamine hydrochloride, 135 g of disodium succinate, and 30 g of polyvinyl-pyrolidone (molecular weight : 10,000) in 1 l of water and adjusted to pH 7.2]containing 1 mg/ml lysozyme and the suspension was shaked gently at 30° C. for 14 hours to make protoplasts Then, 1 ml of the protoplast solution was centrifuged at 2,500×g for 15 minutes to precipitate the protoplast. The protoplast was suspended in 1 ml of TSMC buffer solution (containing 10 mM $MgCl_2$, 30 mM $CaCl_2$, 50 mM Tris-HCl of pH 7.5 and 400 mM sucrose) and washed by centrifugation. The protoplast was resuspended in 0.1 ml of TSMC buffer solution To the suspension were added 20 µl of pAC2 plasmid DNA isolated above, and then 0.8 ml of TSMC buffer solution containing 20% (w/v) polyethyleneglycol (PEG) 6,000. After 3 minutes, 2 ml of RCGP medium was added to the mixture, and the protoplast was precipitated by centrifugation at 2,500×g for 5 minutes. The protoplast was suspended in 1 ml of RCGP medium, and culturing was carried out with gentle shaking at 30° C. for 2 hours 0.1 ml of the protoplast suspension was spread on RCGP agar medium (RCGP medium containing 1.4% agar) containing 400 µg/ml spectinomycin, and cultured at 30° C. for 6 days. Plasmid DNA was extracted from one of the thus obtained spectinomycin-resistant transformants according to the procedure previously disclosed by the present inventors [Japanese Published Unexamined Patent Application No. 134500/82, Example 1, Item (1)]. It was found by the analysis according to the restriction enzyme cleavage and agarose gel electrophoresis that the isolated plasmid had the same structure as that of pAC2. It was also found by the same transformation test as in the foregoing item that the plasmid had the same function to restore the diaminopimelic acid requirement of AT998 strain and AT997 strain as that of pAC2. The strain which was thus confirmed to be transformed by pAC2 was *Corynebacterium glutamicum* RH6/pAC2

(5) Production of L-lysine by pAC2-containing strain

Production of L-lysine by *Corynebacterium glutamicum* RH6/pAC2 strain and parent strain RH6 which do not contain the plasmid was carried out in the following manner.

RH6/pAC2 strain and RH6 strain were separately cultured with shaking in 3 ml of NB medium (a medium containing 20 g of bouillon and 5 g of yeast extract in 1 l of water and adjusted to pH 7.2) at 30° C. for 16 hours Then, 0.5 ml of the cultured broth was inoculated in 5 ml of a production medium Ll [a medium containing 100 g of glucose, 30 g of $(NH_4)2SO_4$, 0.5 g of $KH_2PO_4$, 0.5 g of $K_2HPO_4$, 1 g of $MgSO_4.7H_2O$, 10 mg of $FeSO_4.7H_2O$, 10 mg of $MnSO_4.4-6 H_2O$, 100 µg of biotin, 200 mg of homoserine, and 30 g of calcium carbonate in 1 l of water and adjusted to pH 7.2], and cultured with shaking at 30° C. for 72 hours. After culturing, the L-lysine produced in the filtrate of culture liquid was quantitatively determined by colorimetry according to the acidic copper ninhydrin procedure [Chinard, F. D.: J. Biol Chem 199, 91 (1952)]. The results are shown in Table 1. It is apparent from the Table that the recombinant plasmid pAC2 containing dapA-dapC of *Corynebacterium glutamicum* can enhance the L-lysine productivity of RH6 strain.

TABLE 1

Production of L-lysine by *Corynebacterium glutamicum* RH6 strain and plasmid pAC2-introduced strain

| Strain | L-lysine (mg/ml) |
|---|---|
| *Corynebacterium glutamicum* RH6 | 14.8 |
| *Corynebacterium glutamicum* RH6/pAC2 | 20.0 |

What is claimed is:

1. A process for producing L-lysine which comprises culturing in a medium a microorganism belonging to the genus Corynebacterium or Brevibacterium carrying a recombinant DNA comprising a gene coding for dihydrodipicolinic acid synthase (dapA) isolated from a microorganism belonging to the genus Corynebacterium or Brevibacterium, accumulating L-lysine in the culture broth, and recovering L-lysine therefrom.

2. The process according to claim 1, wherein the microorganism is selected from the group consisting of *Corynebacterium glutamicum, Corynebacterium herculis, Corynebacterium lilium, Corynebacterium acetoacidophilum, Brevibacterium flavum, Brevibacterium lactofermentum, Brevibacterium divaticatum, Brevibacterium immariophilium,* and *Erevibacterium thiogenitalis.*

3. A DNA of which contains a gene coding for dihydrodipicolinic acid synthase (dapA) isolated from a microorganism belonging to the genus Corynebacterium or Brevibacterium.

4. The DNA fragment according to claim 2, wherein the fragment has SalI cleavage sites at both ends thereof, one internal BamHI cleavage site, two internal PvuII cleavage sites, and molecular size of about 4.2 kilobases.

5. A microorganism belonging to the genus Corynebacterium or Brevibacterium, which carries a recombinant vector comprising a gene coding for dihydrodipicolinic acid synthase (dapA) isolated from a microorganism belonging to the genus Corynebacterium or Brevibacterium.

6. *Corynebacterium glutamicum* RH6/pAC2.

* * * * *

UNITED STATES PATENT AND TRADEMARK OFFICE
CERTIFICATE OF CORRECTION

PATENT NO. : 4,954,441
DATED : September 4, 1990
INVENTOR(S) : RYOICHI KATSUMATA ET AL.   Page 1 of 4

It is certified that error appears in the above-identified patent and that said Letters Patent is hereby corrected as shown below:

AT [57] ABSTRACT

Line 3, "dihydropico-" should read --dihydrodipico--.
Line 4, "synthetase," should read --synthase,--.

COLUMN 1

Line 3, insert --This application is a continuation of application Ser. No. 836,989, filed March 6, 1986, now abandoned.--.

COLUMN 2

Line 31, "Nos. 82," should read --Nos. 134500/82,--.
Line 33, "DNA" should read --DNA fragment--.
Line 48, "nucriirgabusn" should read --microorganism--.

COLUMN 3

Line 9, "(1979) Specifically," should read --(1979). Specifically,--.
Line 17, "[hsdR-(host-" should read --[hsdR⁻(host---.
Line 18, "dapA-" should read --dapA⁻--.
Line 51, "shuttletype" should read --shuttle type--.
Line 55, "Japanese" should read --[Japanese--.
Line 56, "Patent Application No. 34500/82]." should read --Patent Application No. 134500/82].--.

UNITED STATES PATENT AND TRADEMARK OFFICE
CERTIFICATE OF CORRECTION

PATENT NO. : 4,954,441

DATED : September 4, 1990

INVENTOR(S) : RYOICHI KATSUMATA ET AL.    Page 2 of 4

It is certified that error appears in the above-identified patent and that said Letters Patent is hereby corrected as shown below:

COLUMN 5

Line 10, "components of" should read --in--.
Line 20, "in the cell" should read
          --components of their cell--.
Line 21, "of DNA." should read --of their DNA.--.

COLUMN 6

Line 1, "embodiment" should read --embodiments--.
Line 7, "mutation:]" should read --mutation--.
Line 12, "(hsdR$^{2-}$)" should read --(hsdR2$^-$)--.
Line 13, "(dapA 16-)" should read --(dapA 16$^-$).
Line 17, "[F-" should read --[F$^-$--.
Line 36, "diaminopimalic" should read --diaminopimelic--.
Line 43, "C600r-m-" should read --C600$_r$-$_m$--- and
          "modificationdeficient" should read
          --modification-deficient--.
Line 44, "*chrichia*" should read --*cherichia*--.

COLUMN 7

Line 9, "K12" should read --K12.--.
Line 19, "chloride" should read --chloride.--.
Line 21, "chloride" should read --chloride.--.
Line 26, "5 minutes" should read --5 minutes.--.
Line 53, "TM103 strain" should read --TM103 strain.--.

UNITED STATES PATENT AND TRADEMARK OFFICE
CERTIFICATE OF CORRECTION

PATENT NO. : 4,954,441
DATED : September 4, 1990
INVENTOR(S) : RYOICHI KATSUMATA ET AL.          Page 3 of 4

It is certified that error appears in the above-identified patent and that said Letters Patent is hereby corrected as shown below:

COLUMN 8

Line 10, "Japan" should read --Japan.--.
    Line 19, "30 ml" should read --30 µl--.
    Line 20, "0 3 units" should read --0.3 units-- and "H20" should read --$H_2O$--.
    Line 34, "pstI" should read --PstI--.
    Line 40, "procedure containing" should read --procedure. ¶ To 120 µl of a reaction solution for SalI containing--.

COLUMN 9

Line 2, "strain.:" should read --strain--.
    Line 10, "$MgCl_2.6H2O$," should read --$MgCl_2.6H_2O$,--.
    Line 16, "pH 7.2]" should read --pH 7.2)--.
    Line 28, "polyvinyl-pyrolidone" should read --polyvinyl-pyrrolidone--.
    Line 40, "solution" should read --solution.--.
    Line 49, "2 hours" should read --2 hours.--.
    Line 68, "RH6/pAC2" should read --RH6/pAC2.--.

UNITED STATES PATENT AND TRADEMARK OFFICE
CERTIFICATE OF CORRECTION

PATENT NO. : 4,954,441

DATED : September 4, 1990

INVENTOR(S) : RYOICHI KATSUMATA ET AL.   Page 4 of 4

It is certified that error appears in the above-identified patent and that said Letters Patent is hereby corrected as shown below:

COLUMN 10

Line 10, "16 hours" should read --16 hours.--.
Line 13, "(NH$_4$)2SO$_4$," should read --(NH$_4$)$_2$SO$_4$,--.
Line 49, "Brevibacterium divaticatum," should read
--Brevibacterium divaricatum,--.
Line 50, "Erevibacterium thiogenitalis." should read
--Brevibacterium thiogenitalis.--.
Line 51, "of which contains" should read
--fragment containing--.
Line 55, "claim 2," should read --claim 3,--.

Signed and Sealed this

Twenty-third Day of June, 1992

Attest:

DOUGLAS B. COMER

Attesting Officer   Acting Commissioner of Patents and Trademarks